(12) United States Patent
Skulachev et al.

(10) Patent No.: US 8,658,624 B2
(45) Date of Patent: Feb. 25, 2014

(54) PHARMACEUTICAL COMPOSITIONS FOR PREVENTING AND TREATING EYE PATHOLOGIES

(75) Inventors: Vladimir P. Skulachev, Moscow (RU); Maxim V. Skulachev, Moscow (RU)

(73) Assignee: Mitotech SA, Luxembourg (LU)

( * ) Notice: Subject to any disclaimer, the term of this patent is extended or adjusted under 35 U.S.C. 154(b) by 848 days.

(21) Appl. No.: 12/445,897

(22) PCT Filed: Oct. 20, 2006

(86) PCT No.: PCT/RU2006/000546
§ 371 (c)(1),
(2), (4) Date: Aug. 31, 2010

(87) PCT Pub. No.: WO2008/048134
PCT Pub. Date: Apr. 24, 2008

(65) Prior Publication Data
US 2010/0323992 A1    Dec. 23, 2010

(51) Int. Cl.
*A61K 31/66*    (2006.01)
(52) U.S. Cl.
USPC ............................ 514/130; 514/912; 514/913
(58) Field of Classification Search
USPC .......................................... 514/130, 912, 913
See application file for complete search history.

(56) References Cited

U.S. PATENT DOCUMENTS

| | | | |
|---|---|---|---|
| 5,538,974 A | 7/1996 | Ogawa et al. | |
| 6,331,532 B1 | 12/2001 | Murphy et al. | |
| 7,029,672 B2 * | 4/2006 | Brancato et al. | 424/94.1 |
| 7,109,189 B2 | 9/2006 | Murphy et al. | |
| 2005/0065099 A1 | 3/2005 | Walkinshaw et al. | |
| 2007/0259908 A1 | 11/2007 | Fujii et al. | |
| 2007/0270381 A1 | 11/2007 | Murphy et al. | |
| 2008/0275005 A1 | 11/2008 | Murphy et al. | |

FOREIGN PATENT DOCUMENTS

| | | |
|---|---|---|
| EP | 1047701 B1 | 5/2005 |
| EP | 1534720 A1 | 6/2005 |
| EP | 1321138 | 4/2006 |
| RU | 2318500 C2 | 3/2008 |
| WO | 9926582 | 6/1999 |
| WO | 2004/014927 A1 | 2/2004 |
| WO | 2006/005759 A2 | 1/2006 |
| WO | 2007046729 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

Adlam et al. (2005) "Targeting an antioxidant to mitochondria decreases cardiac ischemia-reperfusion injury," FASEB J., 19:1088-1095.

Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Anisimov (2007) "Molecular and Physiological Mechanisms of Aging," Antioksidanty, Nov. 27, 2007, [on line] http://imquest.alfaspace.net1BOOK/MFMA/mfma_3_9_2.htm?embedded=yes translated from Russian to English.
Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry, 73(12)1273-1287.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep., 26:231-243.
Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.
Havens et al. (2006) "Regulation of Late G1/S Phase Transition and APCCdh1 by Reactive Oxygen Species," Mol. Cell. Biol., 26(12):4701-4711.
Holloszy (1998) "Longevity of exercising male rats: effect of an antioxidant supplemented diet," Mechanisms of Ageing and Development, 100:211-219.
Zweier et al. (1987) "Direct measurement of free radical generation following reperfusion of ischemic myocardium," PNAS USA, 84:1404-1407.

(Continued)

*Primary Examiner* — Zohreh Fay
(74) *Attorney, Agent, or Firm* — Ann-Louise Kerner; K&L Gates LLP

(57) ABSTRACT

The present invention relates to pharmacology, medicine, opthalmology, and, in particular, concerns a class of chemical compounds of structure (I) and also their solvates, isomers or prodrugs applicable when incorporated into pharmaceutical compositions also containing pharmaceutically acceptable carrier which can be useful for prophylaxis and treatment of different eye pathologies such as cataract and macular dystrophy.

11 Claims, 4 Drawing Sheets

(56) References Cited

OTHER PUBLICATIONS

Kirschner et al. (1994) "Role of iron and oxygen-derived free radicals in ischemia-reperfusion injury" J. Am. Coll. Surg., 179:103-117.

Li et al. (2000) "Skeletal muscle respiratory uncoupling prevents diet-induced obesity and insulin resistance in mice," Nat. Med. 6(10):1115-1120.

Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.

Longo et al. (2005) "Programmed and altruistic ageing," Nature Reviews Genetics, 6:866-872.

Lou et al. (2007) "Mitochondrial Uncouplers With an Extraordinary Dynamic Range," Biochem. J., 407:129-140.

Mecocci et al. (2000) "Plasma antioxidants and longevity: a study on healthy centenarians," Free Radical Biology and Medicine, 28(8):1243-1248.

Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.

Orr et al. (2003) "Effects of overexpression of copper-zinc and manganese superoxide dismutases, catalase, and thioredoxin reductase genes on longevity in *Drosophila melanogaster*," J. Biol. Chem., 278(29):26418-26422.

Sundaresan et al. (1995) "Requirement for Generation of H2O2 for Platelet-Derived Growth Factor Signal Transduction," Science, 270:296-299.

Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.

Petrosillo et al. (2006) "Protective effect of melatonin against mitochondrial dysfunction associated with cardiac ischemia-reperfusion: role of cardiolipin," FASEB J., 20:269-276.

Popova et al. (2006) "MitoQ induced miofibroblast differentiation of human fibroblasts," Biochimica et Biophysica Acta, S:433-434.

Popova et al. (2010) "Scavenging of Reactive Oxygen Species in Mitochondria Induces Myofibroblast Differentiation," Antiox. & Redox. Signal., 13(9):1297-1307.

Pozniakovsky et al. (2005) "Role of mitochondria in the pheromone- and amiodarone-induced programmed death of yeast, "J. Cell Biol., 168(2):257-69.

Reddy (2006) "Mitochondrial oxidative damage in aging and Alzheimer's disease: implications for mitochondrially targeted antioxidant therapeutics," J. Biomedicine and Biotech., Art.ID 31372:1-13.

Reliene et al. (2007) "Antioxidants suppress lymphoma and increase longevity in atm-deficient mice," J. Nutrition, 137:229S-232S.

Riess et al. (2004) "Reduced reactive O2 species formation and preserved mitochondrial NADH and [Ca2+] levels during short-term 17° C. ischemia in intact hearts," Cardiovascular Research, 61:580-590.

Skulachev (2007) "A Biochemical Approach to the Problem of Aging: 'Megaproject 'on Membrane-Penetrating Ions. The First Results and Prospects," Biochem. (Moscow), 72(12):1385-1396.

Sheu et al. (2006) "Targeting antioxidants to mitochondria: a new therapeutic direction," Biochimica et Biophysica Acta, 1762:256-265.

Sidorova et al. (2004) "Transcriptional activation of cytochrome P450 1A1 with alpha-tocopherol," Bull Exp. Bio. Med., 138(3):233-236.

Skulachev (2005) "Critical Review: How to Clean the Dirtiest Place in the Cell: Cationic Antioxidants as Intramitochondrial ROS Scavengers," IUBMB Life, 57(4/5):305-310.

Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.

Tompkins et al. (2006) "Mitochondrial dysfunction in cardiac ischemia-reperfusion injury: ROS from complex I, without inhibition," Biochim. Biophys. Acta. 1762:223-231.

Starkov et al. (1997) "6-ketocholestanol is a recoupler for mitochondria, chromatophores and cytochrome oxidase proteoliposomes," Biochim. Biophys. Acta. 1318:159-172.

International Search Report and Written Opinion, PCT/RU2009/000621, dated Aug. 12, 2010, 12 pages.

International Search Report dated Dec. 20, 2007 and International Preliminary Report on Patentability dated Nov. 10, 2009, PCT/RU2007/000171 (16 pages).

International Search Report, PCT/RU2008/000706, Aug. 13, 2009 (3 pages).

International Search Report and Written Opinion of the International Searching Authority, PCT/RU2007/000044, Nov. 1, 2007, 9 pages.

International Search Report and Written Opinion of the International Searching Authority, PCT/RU2007/000355, Mar. 27, 2008 (10 pages).

PCT International Search Report mailed Nov. 1, 2007 and International Preliminary Report on Patentability issued Aug. 4, 2009 for PCT Application No. PCT/RU2007/000043, 9 pages.

International Search Report and Written Opinion of the International Searching Authority, PCT/RU2009/000295, Feb. 25, 2010, 7 pages.

PCT International Search Report and Written Opinion of the International Searching Authority for PCT Application No. PCT/RU2006/000546, mailed Jul. 5, 2007, 14 pages.

International Search Report and Written Opinion, PCT/RU2006/000547, dated Jul. 5, 2007 (7 pages).

International Search Report and Written Opinion, PCT/RU2006/000394, dated Nov. 2, 2006 (6 pages).

Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.

Clem et al. (2008) "Small-molecule inhibition of 6-phosphofructo-2-kinase activity suppresses glycolytic flux and tumor growth," Mol. Canc. Ther. 7(1):110-120.

Goldstein (2002) "Reactive oxygen species as essential components of ambient air," Biochemistry (Mosc.) 67:161-170.

Green (1974) "The electromechanochemical model for energy coupling in mitochondria," Biochimica et Biophysica Acta, 346:27-78.

Kirste et al. (1995) "Continuous-wave electron spin resonance studies of porphyrin and porphyrin-quinone triplet states," J. Chem. Soc. Perkin Trans. 2:2147-2152.

Murphy et al. (2007) Targeting antioxidants to mitochondria by conjugation to lipophilic cations. Annu. Rev. Pharmacol. Toxicol., 47:629-656.

Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.

Plotnikov et al. (2010) "New-generation Skulachev ions exhibiting nephroprotective and neuroprotective properties." Biochemistry (Mosc.), 75(2):145-150.

Skulachev et al. (2005) "Aging as mitochondria-mediated atavistic program. Can aging be switched off?" Ann. N.Y. Acad. Sci., 1057:145-164.

Skulachev et al. (2009) "An attempt to prevent senescence: a mitochondrial approach," Biochimica et Biophysica Acta., 1787:437-461.

Smith et al. (2008) "Mitochondria-targeted antioxidants in the treatment of disease,"Ann. N.Y. Acad. Sci., 1147:105-111.

Snow et al. (2010) "A double-blind, placebo-controlled study to assess the mitochondria-targeted antioxidant MitoQ as a disease-modifying therapy in Parkinson's disease," Mov. Disord. 25(11):1670-1674.

Stefanova et al. (2010) "Behavioral effects induced by mitochondria-targeted antioxidant SkQ1 in Wistar and senescence-accelerated OXYS rats," J. Alzheimer's Dis. 21:479-491.

Tauskela (2007) "MitoQ—a mitochondria-targeted antioxidant," IDrugs, 10:399-412.

(56) References Cited

OTHER PUBLICATIONS

Triet et al. (1993) "Anxiogenic stimuli in the elevated plus-maze," Pharmacol. Biochem. & Behav. 44:463-469.
PubChem compound CID 388445; Mar. 26, 2005 [retrieved from http://pubchem.ncbi.nlm.nih.gov/summary/summary.cgi?cid=38845&loc=ec_rcs on Jul. 31, 2012] whole doc (4 pages).
International Search Report and Written Opinion of the International Searching Authority, PCT/US12/40711, Aug. 20, 2012 (9 pages).
Bacsi et al., "Effect of pollen-mediated oxidative stress on immediate hypersensitivity reactions and late-phase inflammation in allergic conjunctivitis," J. Allergy Clin. Immunol., 116(4): 836-843 (2005).
Emiko et al., "Manganese Superoxide Dismutase protects against oxidation-induced apoptosis in mouse retinal pigment epithelium: implications for age-related macular degeneration," Invest. Ophthalmol. Vis. Sci., 46(9): 3426-3434 (2005).
King et al., "Mitochondria-derived reactive oxygen species mediate blue light-induced death of retinal pigment epithelial cells," Photochem. and Photobiol, 79(5): 470-475 (2004).
Lysenko et al., "Thrombocytopathies and their role in the development of hemorrhagic syndrome in vascular diseases of the fundus oculi," Vestn. Oftalmol., 117(1): 24-26 (2001).
Papp et al., "Glutathione status in retinopathy of prematurity," Free Radic. Biol. Med., 27(7-8): 738-743 (1999).
Spector, "Oxidative stress-induced cataract: mechanism of action," FASEB J., 9(12): 1173-1182 (1995).
Yildirim et al., "Role of oxidative stress enzymes in open-angle glaucoma," Eye, 19(5): 580-583 (2005).

* cited by examiner

PHARMACEUTICAL COMPOSITIONS FOR PREVENTING AND TREATING EYE PATHOLOGIES

FIELD OF THE INVENTION

This invention relates to pharmacology, medicine, opthalmology, and, in particular, concerns a class of chemical compounds of structure (I) which being incorporated into pharmaceutical compositions can be used for prophylaxis and treatment of different eye pathologies such as cataract and macular dystrophy.

BACKGROUND

At present, various methods of treatment of eye pathologies—surgical and medicamental, are applied in medical practice. Medicamental methods usually comprise natural and synthetic compounds possessing antioxidant properties (antioxidants).

In pathogenesis of many eye pathologies (including cataract and macular dystrophy), the oxidative stress—disruption of the balance between production of free radicals and their elimination by antioxidants, plays an important role.

Only bioactive nutrients containing natural carotenoids possessing antioxidant properties—lutein and zeaxanthin have been available in Russia to date. Said compounds also contain plant carotenoid beta-carotene (1.5 mg) that plays an important role in the formation of a visual pigment rhodopsin providing an eye with adaptation to the lowered lighting; antioxidants—vitamins E and C, micronutrients zinc and copper which are also important to maintain the health of eyes.

Age-related macular degeneration (AMD) occupies a highly important place in the world among disorders leading to persistent deterioration of visual functions and blindness (J. Evans, C. Rooney, F. Ashood, 1996). AMD is one of the eye diseases which are difficult to treat (L. N. Marchenko, 2001). The Russian Central Scientific Research Institute of Expertise of Work Capability and Organization of Labor of the Disabled reported in 1997 that the vascular diseases of retina resulting in eye disability in particular comprise non-exudative age-related macular degeneration—39.4%, exudative age-related macular degeneration—9.1%, bloodstream disruption in great retina vessels—51.5%. Age-related macular degeneration constituted about 10% of blindness registered in the Western Europe 25 years ago, this value has increased up to 50% to date (V. S. Akopyan, 2004). According to the reports of WHO/OMS (1986), increase in proportion of elders within the human population leads to annual increase in said disease. The history of macular degeneration problem originated from 1855 when F. S. Donders described macular drusen. The term "senile macular degeneration" was first introduced by O. Haab in 1885. Later on, C. Behr (1920) and H. F. Falls (1949) assigned said pathology to hereditary familial diseases. Taking into account a variety of clinical and opthalmoscopic data, different terms have been applied to age-related macular degeneration in the literature. To date a consensus exists among ophthalmologists that all these pathology types are a manifestation of the same disease that now is often designated in the literature as "age-related macular degeneration" (AMD).

AMD is a pathology of central photoactive area of retina. The disease is a chronic dystrophic process when choriocapillaries, Bruch's membrane and pigment retinal epithelium are predominantly affected followed by the affection of photoreceptors (V. S. Lysenko et al., 2001). The extent of the process severity and the loss of central vision depends on AMD type and vicinity of dystrophic process to central fossa of retina. AMD is most commonly double-sided process. The second eye was observed to be affected within 5 years after the affection of the first eye (H. C. Zweng, 1977).

Progression of macular degeneration results in increased light sensitivity, eyesight degradation, gradual loss of eyeshots, and finally appearance of turbid spot in the center of visual field (relative or absolute scotoma). The reasons resulting in macular degeneration are different. However the role of genetic factors and damaging action of light are undoubted. At present, the consequences of negative effect of free oxygen radicals are often discussed in the scientific literature. Photochemical reaction induced by light and oxygen results in the formation of highly reactive free radicals which are capable for damaging light sensitive cells of eye retina. The older is a person, the more dangerous is the effect of free radicals—natural aging correlates with decline of the activity of intrinsic protective antioxidant system of an organism that accelerates dystrophic processes.

Prolonged computer work also leads to eyesight degradation. Computer monitor is a source of serious hazard to eyes since it radiates ultraviolet light, the effect of the latter is enhanced when luminescent lamps are used. Coupled with hard work of eyes, this can cause fast exhaustion, headaches, decrease in capability for work, eye pain, lachrymation. According to statistics, from 50% to 90% of persons engaged in computer working have such complaints when see a doctor. These complaints are combined into the term "computer vision syndrome". To increase antioxidant protection of eyes, persons engaged in computer working need additional administration of antioxidants.

Vitamins-antioxidants such as vitamins C and E, bioflavonoids, beta-carotene also protect eyes from damaging and facilitate anabolic processes supporting collagen biosynthesis. Combined administration of N-acetyl-cysteine, lipoic acid and vitamins C and E stimulates biosynthesis of antioxidant enzymes of eye tissue, glutathione.

DESCRIPTION

One of the aspects of the present invention is a pharmaceutical composition for prophylaxis and treatment of different eye pathologies comprising a compound that includes targeting moiety, linker group and antioxidant. In general, such a compound can be described by the following structure (I):

(structure I)

wherein A is an effector—antioxidant of structure:

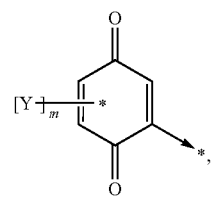

and/or reduced form thereof, wherein m is an integer from 1 to 3; each Y is independently selected from the group consisting of: lower alkyl, lower alkoxy; or two adjacent Y groups, together with carbon atoms to which they are attached form the following structure:

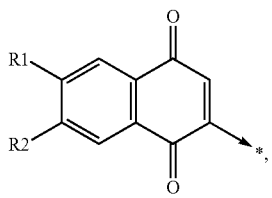

and/or reduced form thereof,
wherein R1 and R2 may be the same or different and are each independently lower alkyl or lower alkoxy;
L is a linker group, comprising:
a) straight or branched hydrocarbon chain optionally substituted with one or more substituents and optionally containing one or more double or triple bonds; or
b) natural isoprene chain; and
n is integer from 1 to 20;
B comprises:
a) a Skulachev-ion Sk:

$Sk^+Z^-$ where Sk is a lipophilic cation, and Z is a pharmacologically acceptable anion; and/or
b) a charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol or a mimetic of superoxide dismutase or ebselen; when L is neither divalent decyl nor divalent pentyl nor divalent propyl radical; and when B is triphenylphosphonium cation; including solvates, isomers or prodrugs thereof.

A further aspect of the present invention is a pharmaceutical composition for prophylaxis and treatment of different eye pathologies comprising a compound of structure (I), wherein A is a plastoquinone of structure:

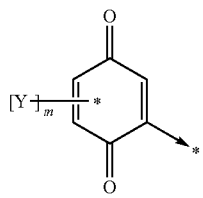

wherein Y is methyl, m=2;
L is a linker group, comprising:
a) straight or branched hydrocarbon chain optionally substituted with one or more substituents and optionally containing one or more double or triple bonds; or
b) natural isoprene chain;
n is integer from 1 to 20;
B comprises:
a) a Skulachev-ion Sk:

$Sk^+Z^-$ where Sk is a lipophilic cation, and Z is a pharmacologically acceptable anion; and/or
b) a charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol nor mimetic of superoxide dismutase or ebselen; when L is neither divalent decyl nor divalent pentyl nor divalent propyl radical; and when B is triphenylphosphonium cation; including solvates, isomers or prodrugs thereof.

A further aspect of the present invention is a pharmaceutical composition for prophylaxis and treatment of different eye pathologies comprising a compound of structure (I)—SkQ1:

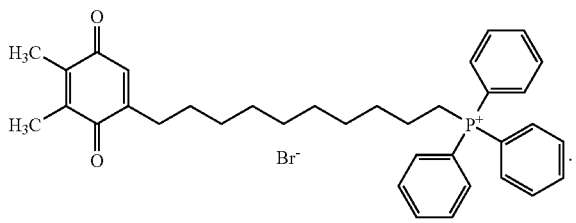

A further aspect of the present invention is a pharmaceutical composition for prophylaxis and treatment of different eye pathologies comprising therapeutically or prophylactically justified amount of a compound of Structure (I) and at least one pharmacologically acceptable solvent or carrier. A pharmacologically acceptable solvent or carrier may present a filler, a diluent (solvent) or their mixture. "Therapeutically justified" amount of a compound is amount of a compound of Structure (I) that causes desired biological or medical response in a patient treated by a doctor or a veterinarian. "Prophylactically justified" amount of a compound is amount of a compound of Structure (I) that prevents or suppresses the disease, or relieves progress of the disease in a patient suffering from a medical state that is tried to be prevented, suppressed or relieved by a doctor or a veterinarian.

A patient is a human in one of the aspects of the present invention.

"Eye pathologies" comprise but are not limited by: different forms of macular degeneration (MD) and other related symptoms, namely: atrophic (dry) MD, exudative (wet) MD, age-related macular retinopathy (ARM), choroidal neovascularization, detached pigment retinal epithelium (PED), atrophy of pigment retinal epithelium (RPE). The term "macular degeneration (MD)" also comprises all eye diseases irrelevant to age-related changes in a human organism, namely: vitelliform degeneration of Best, Stargardt disease, juvenile macular dystrophy, Behr's disease, Sorsby's dystrophy, Doyne honeycomb retinal dystrophy. "Symptoms related to macular degeneration" comprise but are not limited by: drusen surrounded by white-yellow spots, submacular discoid scar of tissues, choroidal neovascularization, detached pigment retinal epithelium (PED), atrophy of pigment retinal epithelium (RPE), anomalous expansion of choroidal blood vessels, blurred or disturbed vision area, central dead point, pigment anomalies, mixed layer of thin granulation located on the inner side of Bruch's membrane, thickening and lowered permeability of Bruch's membrane.

Said compositions are particularly useful for treatment and/or prophylaxis of such disorders as: cataract including senile cataract, diabetic cataract, retinopathy, detached retina, pathology of retinal vessels, eye vascular envelope, optic nerve including atrophy of optic nerve, central and peripheral chorioretinal dystrophies, in particular, uveitis; intraocular hemorrhage, traumatic hemorrhage; conjunctivitis; ophthalmic ulcer; keratitis including filamentary keratitis; glaucoma.

The reasons causing macular degeneration include but are not limited by: genetic or physical trauma, diseases such as diabetes, or infections, in particular, bacterial.

The compounds of structure (I) can be applied to efficient prophylaxis and therapy of all forms of macular degeneration (MD) and other MD related syndromes or symptoms irrespective of the reasons which have caused them.

Application of the pharmaceutical compositions of the present invention can be both somatic and local. Administration methods comprise enteral such as oral, sublingual and rectal; local such as through-dermal, intradermal and oculodermal; and parenteral. Acceptable parenteral methods of administration comprise injections, for example, intravenous, intramuscular, hypodermic injections et cetera, and noninjection methods such as intravaginal and nasal. Per ocular or per oral administration of the compounds and the pharmaceutical compositions of the present invention is more preferable. In particular, the administration can be carried out in the form of eye drops or tablets, granules, capsules or other pressed or compressed form.

When a compound of structure (I) is administered as a pharmaceutical composition, the compound of structure (I) should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with the compound of structure (I) for administration to a patient. Liquors like water, and oils including petrolic, animal, vegetative and synthetic such as peanut oil, soybean oil, mineral oil and other similar oils can be used as said pharmacological carriers. Normal saline solution, acacia pitch, gelatin, starch, talc, keratin, colloid silver, urea etc can serve as said pharmacological solvents.

Said composition can also include auxiliary substances, stabilizers, thickeners, lubricant and coloring agents.

The compounds and compositions of the present invention can be administered in the form of capsules, tablets, pills, pillets, granules, syrups, elixirs, solutions, opthalmologic solutions, suspensions, emulsions, suppositories or retarded release substances, or in any other form suitable for administration to a patient.

One of the aspects of the present invention is application of the compounds of structure (I) and compositions in the form of solutions for per oral and per ocular administration.

Therapeutically justified amount of a compound of Structure (I) required for treatment of a specific disease or symptom, depends on the nature of disease or symptom and a method of administration and should be determined at consultation with a physician in charge. In principle, upon per oral administration, acceptable doses are from 1 to 500 µg/kg of a patient body weight, 25 µg/kg of a patient body weight is more preferable, and 125 µg/kg of a patient body weight is the most preferable.

Example of Pharmaceutically Acceptable Composition in the Form of Solution for Per Oral Administration.
  10 mM sodium phosphate buffer, pH 6.0
  SkQ1 at concentration of 125 µg/mL
  Aqueous solution
An Example of Pharmaceutically Acceptable Composition in the Form of Opthalmologic Solution (Eye Drops).
  10 mM sodium phosphate buffer, pH 6.5
  Aqueous solution of 250 nM SkQ1
  Aqueous solution of 0.9% NaCl

Figure 1:
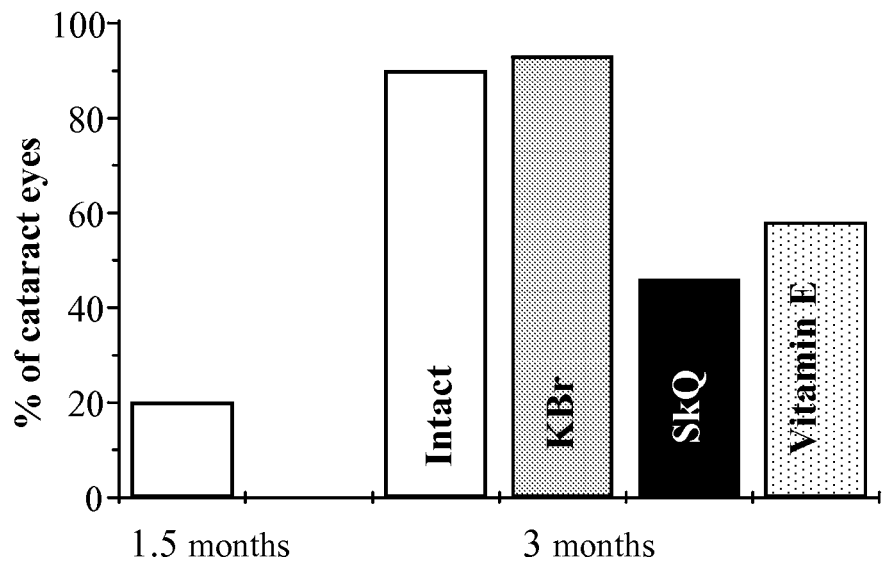
FIG. 1 shows the influence of the compounds on the cataract morbidity in OXYS rats.

The following non-limiting Examples illustrate the preparation and use of the compounds of structure I but should not be understood as limiting the invention as modifications in materials and methods will be apparent to the skilled person. The following examples should not be construed as limiting the scope of this disclosure.

EXAMPLES

1. Prophylactic Effect of SkQ1 Antioxidant of the Present Invention Against Age-Related Eye Diseases The study was carried out using OXYS and Wistar male rats. The animals were housed in cages (five rats per a cage) and kept under standard laboratory conditions (at 22±1° C., 60% relative humidity, and natural light), provided with a standard rodent diet (PK-120-1, Ltd. 'laboratorsnab', Russia), and given water ad libitum. At the age of 1.5 months after preliminary pupil dilation with 1% tropicamide ophthalmic the rats were examined by ophthalmologist. During the period from 1.5 to 3 months, which is critical for the development of pronounced changes in eye organ of OXYS rats, the animals were given either SkQ1 (50 nmol per kg of body weight), or KBr (50 nmol per kg of body weight) or vitamin E (alfa-tocopherol acetate, 20 mg per kg). We use Vitamin E for a comparison with test antioxidants. Animals received the compounds on a small piece of dried bread before a regular meal, and the control group of animals received the same piece of bread without any compound. After completing the course of antioxidants the animals were weighed and retested with opthalmoscope. To avoid human factor in the evaluation of compound effects, the researcher who conducted the opthalmoscopic examination was not told which of the animals received antioxidants.

The opthalmoscopic examination was carried out using direct opthalmoscope "Betta", Germany. In selected animals under fluorotane narcosis (1-1.5 minutes) eyeground was photographed, fluorescent angiography with the use of "Opton" fundus-camera was conducted or crystalline lenses were examined by means of slitlamp "Opton SL30" using system of automatic image registration (biomicroscopic research).

The lens state was evaluated according to the classification system accepted in clinical practice (L. A. Katsnelson, T. I. Forofonova, A. Ya. Bunin, 1990) with grades ranging from 0 to 3: score 0—the lens is clear; score 1—spotted weak cloudiness; score 2—multiple spots of cloudiness and score 3—intense cloudiness of the lens core and nucleus. The presence and the degree of spotted changes in macular area were evaluated according to accepted classification: score 0—no changes; score 1—the 1st stage of pathology, when small yellow deposits, known as "drusen" appear underneath the macula; score 2—2nd stage, the development of prominent yellow spot with sharp edges with the size of 0.5 to 1 of the disk diameter (exudative detachment of pigment retinal epithelium); and score 3—3rd stage with extensive hemorrhage into macular area.

Statistical processing of the results was carried out using the factorial dispersive analysis (ANOVA/MANOVA, Statistica, 5) with post hoc comparison of group average (Newman-Keul test) considering genotype and preparation as independent factors.

Results Obtained

Opthalmoscopic examination did not reveal any changes in the lenses or in the macular area of the retina in 1.5 and 3 month-old Wistar rats. In contrast, in OXYS rats early cataract (score 1) was observed in 20% of cases (FIG. 1) and macular degeneration of the 1st stage—in 10% of cases at the age of 1.5-months (FIG. 2).

At the age of 3 months in the control intact group of OXYS rats pathological changes of lenses were observed in 90% of examined eyes, including 35% of eyes with 2nd stage of cataract, with ring-shaped and nuclear cataracts prevailed (FIG. 1).

Figure 2:
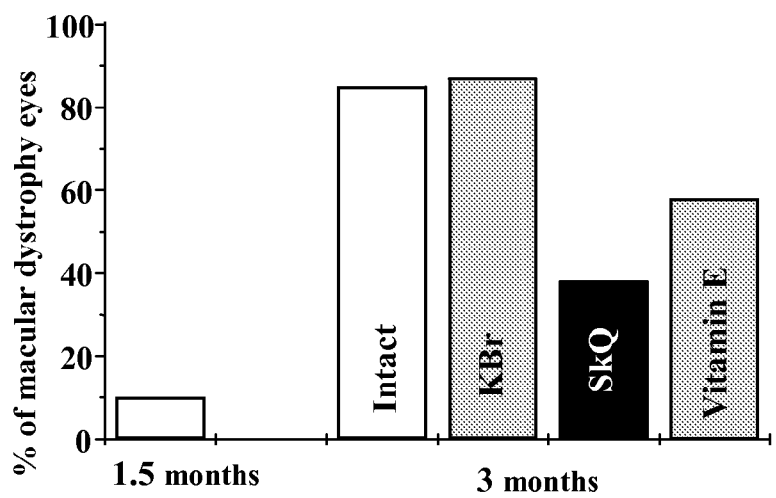
FIG. 2 demonstrates the influence of the compounds on the macular dystrophy morbidity in OXYS rats.

Macular dystrophy was observed in 85% of eyes from control group of animals of which 16% corresponded to the 2nd stage of this pathology (FIG. 2). In the group of OXYS rats supplemented with KBr, lens changes were observed in 93% of eyes, with 57% of total number of eyes having 2nd stage of cataract progression. Changes in the macular area of the retina were observed in 87% of eyes of animals from this group and 13% of these changes corresponded to the 2nd stage of the disease. Taking into account that cataract already affected 20% of eyes, 73% of rat eyes have been newly affected, and respectively macular dystrophy has affected 77% of eyes.

In animals supplemented with SkQ1 (FIG. 1) some lens changes were registered in 46% of cases, however these changes corresponded to the 1st stage of cataract. Changes in the macular area of the retina in OXYS rats of this group were revealed in 38% of cases and also were defined as the 1st stage of macular degeneration (FIG. 2). Of this group of rats supplemented with SkQ1, cataract was revealed in 26% of cases (2.8 times less than in the group of rats supplemented with KBr), macular dystrophy was detected in 28% of cases (also 2.8 times less than in the control group).

Figure 3:
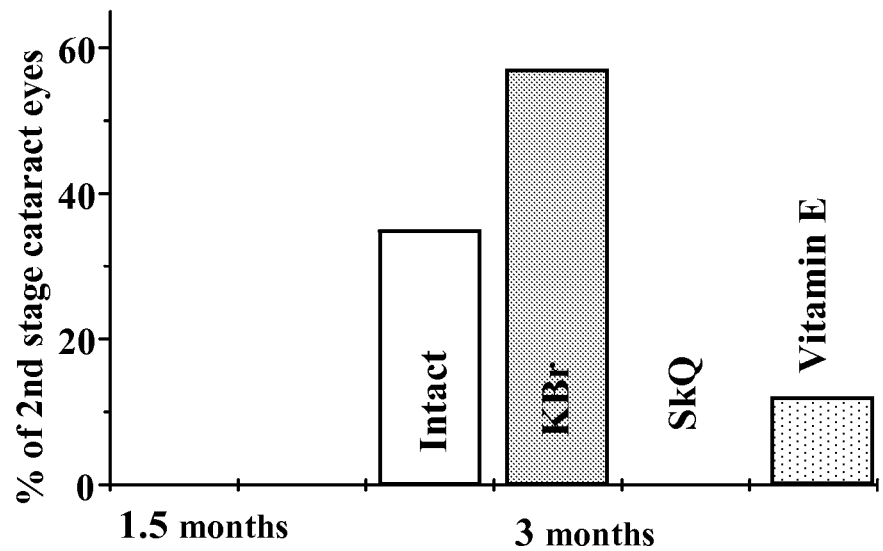
FIG. 3 shows the influence of the compound on the cataract progression in OXYS rats.
Figure 4:
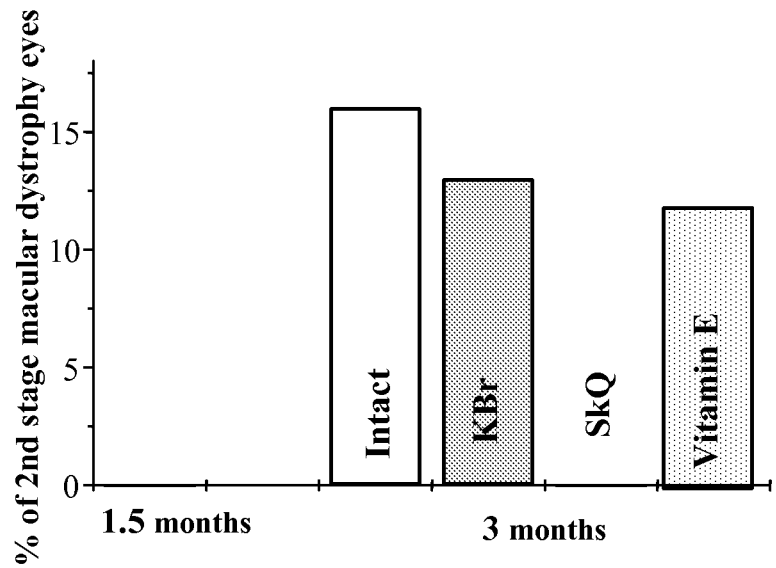
FIG. 4 shows the influence of the compound on the macular degeneration progression in OXYS rats.
Figure 5:
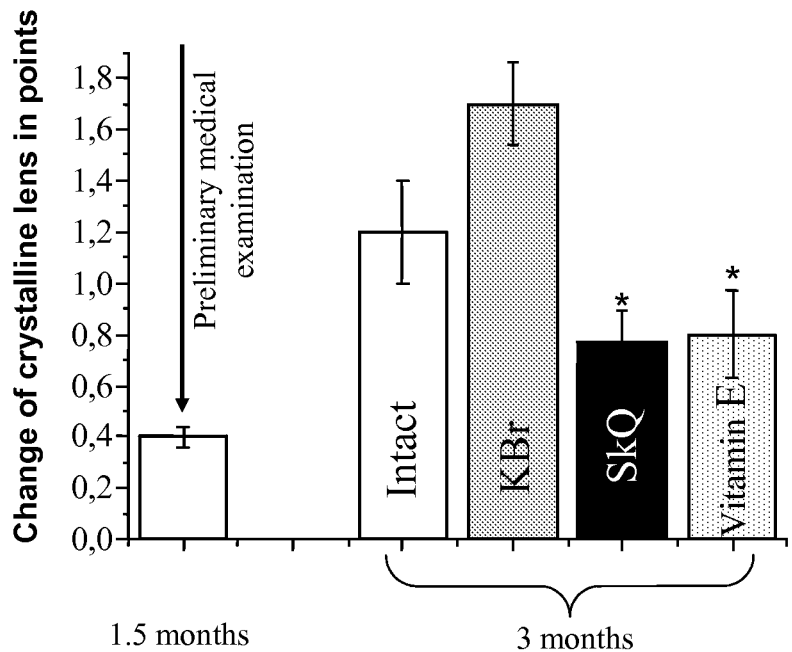
FIG. 5 compares the state of crystalline lens of OXYS rats before administering and after 45-day course of KBr, SkQ1 or vitamin E.
Figure 6:
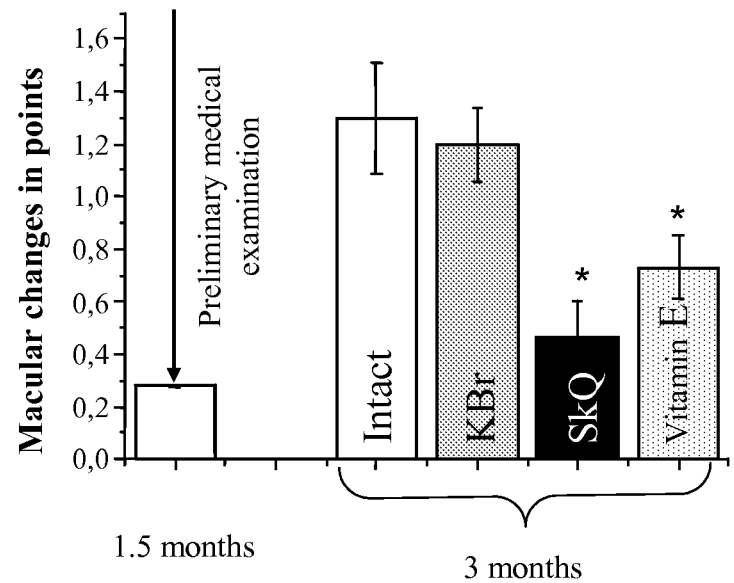
FIG. 6 shows degenerative changes in macular region of retina of OXYS rats before administering and after 45-day course of KBr, SkQ1 and vitamin E.

In the group of rats supplemented with vitamin E, lens changes were registered in 58% of cases (38% has been added, 1.8 times less than in the control intact group), with 12% of changes corresponding to the 2nd stage of the cataract. Changes in the macular area of the retina were revealed in 54% of OXYS rats from this group (1.5 times less than in the control intact group), including 8% corresponding to the 2nd stage of macular degeneration. Administration of SkQ1 not only decreased the cataract and macular dystrophy morbidity but also essentially affected their progression (see FIG. 3 and FIG. 4 respectively).

It is remarkable that in one month after the end of the course of SkQ1 administration, no any changes in the state of retina and crystalline lens of the rats supplemented with SkQ1 have been observed, in contrast to the control group of animals.

Thus, the investigations performed prove the efficiency of SkQ1 application for prophylaxis of age-related eye diseases including prophylaxis of cataract and macular dystrophy—the main age-related eye pathologies in elders.

2. Therapeutic Effect of SkQ1 Antioxidant of the Present Invention Against Age-Related Eye Diseases The experiment followed the same pattern as said investigation demonstrating prophylactic effect of SkQ1 except that in this experiment OXYS and Wistar rats at the age of 10.5 months were used.

Results

Table 1 shows the results of examination of animals before administering at the age of 10.5 months and after the therapy course. In Wistar rats, changes of crystalline lenses and retina exceeding characteristic parameters for the appropriate age were revealed that is due to specific conditions of cage keeping of these animals. Examination of Wistar rats in 45 days did not reveal any changes in the state of crystalline lenses, the compounds also did not affect substantially the state of lenses. Among Wistar rats supplemented with SkQ1, animals with changes of retina which could be qualified as appropriate to even the most initial stage of disease were practically absent.

Figure 7:
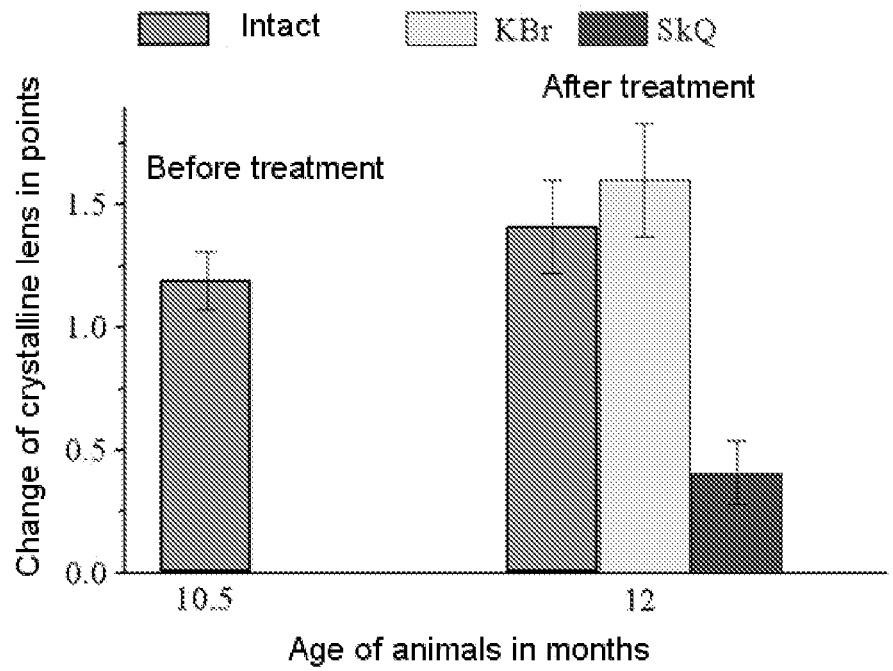
FIG. 7 demonstrates the therapeutic effect of SkQ1 on the state of crystalline lens of OXYS rats.
Figure 8:
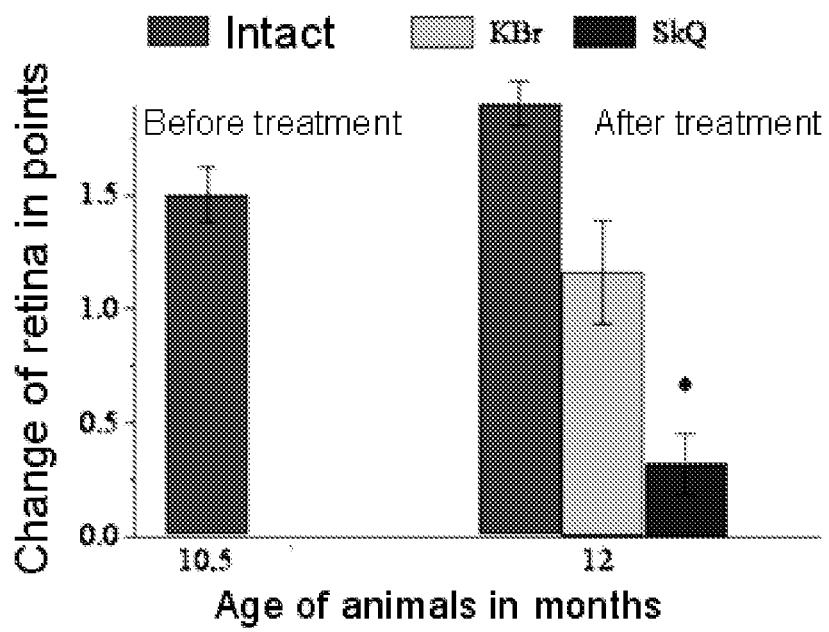
FIG. 8 demonstrates the therapeutic effect of SkQ1 on the state of retina of OXYS rats.

Pair comparisons showed that in the control intact group of OXYS rats, pathological changes of lenses and retina for 1.5 months have authentically aggravated ($p<0.04$ and $p<0.01$ accordingly). In animals supplemented with KBr, changes of lenses have authentically aggravated whereas no any changes of retina have been observed. It should be emphasized that the state of eyes before and after the therapy course has been compared therefore when the average values are compared (Table 1, FIGS. 7 and 8), in OXYS rats supplemented with SkQ1 these pathological changes have really been much less pronounced. In retina of this group of animals, significant reduction of puffiness was observed; there was also reduction of quantity and area of ischemic centers, resolution of hemorrhages.

TABLE 1

The state of animal eyes before and after course of SkQl (50 nmol per kg of body weight). Changes of lenses and macular area of retina are given with grades (score).

| | Preliminary examination at the age of 10.5 months | Examination after therapy course at the age of 12 months | | |
|---|---|---|---|---|
| | | Intact | KBr | SkQl |
| | | OXYS | | |
| Macular | 1.46 ± 1.18 | 1.90 ± 0.10 | 1.13 ± 0.17 | 0.32 ± 0.13 |
| Lenses | 1.19 ± 0.12 | 1.41 ± 0.19 | 1.6 ± 0.23 | 0.41 ± 0.13 |
| | | Wistar | | |
| Macular | 0.48 ± 0.19 | 0.5 ± 0.25 | 0.25 ± 0.10 | 0.09 ± 0.06 |
| Lenses | 0.40 ± 0.23 | 0.5 ± 0.22 | 0.5 ± 0.15 | 0.54 ± 0.14 |

The data obtained proves the therapeutic effect of SkQ1-based pharmaceutical composition on animals suffering from cataract or retinopathy corresponding to macular dystrophy of retina in humans.

The invention claimed is:

1. A method of treating an eye pathology in a mammal, comprising administering to the mammal a therapeutically effective amount of SkQ1:

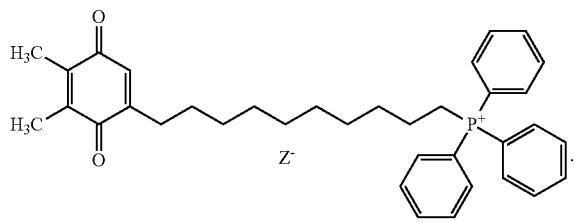

2. The method of claim 1, wherein the pharmaceutical composition is a solution and is orally administered.

3. The method of claim 1, wherein the pharmaceutical composition is an ophthalmologic solution and is ocularly administered.

4. The method of claim 1, wherein the pharmaceutical composition is a solution which is parenterally administered.

5. The method of claim 1, wherein the mammal being treated is human.

6. The method of claim 1, wherein the pathology is macular dystrophy of the retina.

7. The method of claim 1, wherein the pathology is cataract, senile cataract, or diabetic cataract.

8. The method of claim 1, wherein the pathology is retinopathy, detached retina, pathology of the retinal vessels, pathology of the eye vascular envelope, atrophy of the optic nerve, central or peripheral chorioretinal dystrophies, or uveitis.

9. The method of claim 1, wherein, the pathology is an intraocular hemorrhage or traumatic hemorrhage.

10. The method of claim 1, wherein the pathology is conjunctivitis, ophthalmic ulcer, keratitis, or filamentary keratitis.

11. The method of claim 1, wherein the pathology is glaucoma.

* * * * *